United States Patent [19]

Lau

[11] Patent Number: 4,587,315
[45] Date of Patent: May 6, 1986

[54] DIETHYNYLATED PHENYLBENZIMIDAZOLE COMPOUNDS

[75] Inventor: Kreisler S. Y. Lau, Alhambra, Calif.

[73] Assignee: Hughes Aircraft Company, Los Angeles, Calif.

[21] Appl. No.: 735,926

[22] Filed: May 20, 1985

Related U.S. Application Data

[62] Division of Ser. No. 655,009, Sep. 26, 1984, Pat. No. 4,537,974.

[51] Int. Cl.$^4$ ............................................. C08F 14/18
[52] U.S. Cl. ..................................... 526/247; 526/248
[58] Field of Search ........................................ 526/248

[56] References Cited

U.S. PATENT DOCUMENTS 3,817,749 6/1974 Kitahara et al. ..................... 526/259

Primary Examiner—Harry Wong, Jr.
Attorney, Agent, or Firm—M. E. Lachman; A. W. Karambelas

[57] ABSTRACT

A diethynylated phenylbenzimidazole compound having the formula:

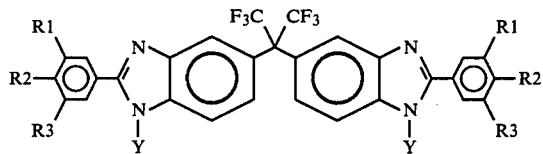

where Y is phenyl, cyclohexyl, adamantyl or phenoxylatedphenyl of the formula $C_6H_5(OC_6H_4)n$ (n=1 to 3) and where R1, R2 and R3 are ethynyl, phenoxyethynyl, phenylethynyl, or hydrogen, and further wherein at least one of said R1, R2 or R3 is not hydrogen. The compounds can be cured to form thermoset polymers which are stable at temperatures above 300° C.

3 Claims, 1 Drawing Figure

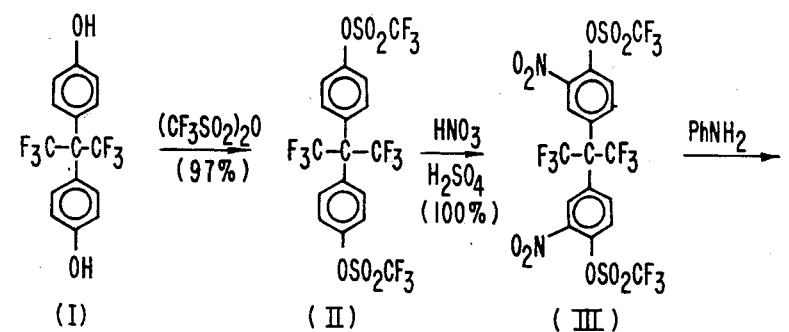
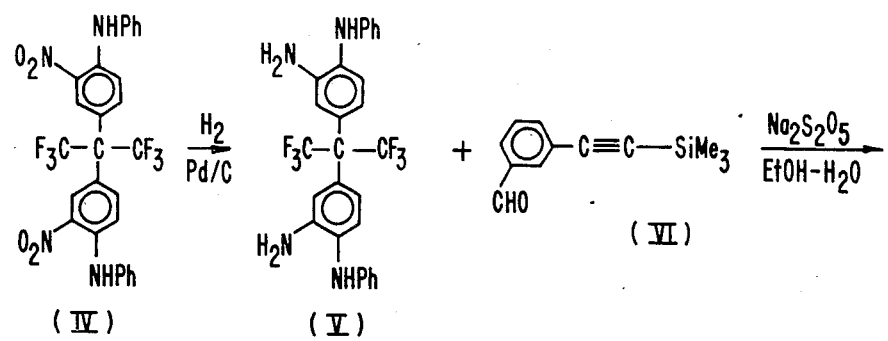
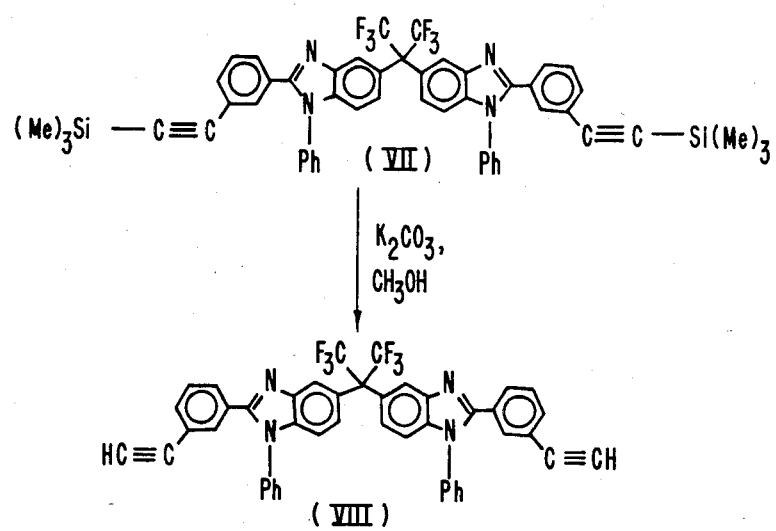

DIETHYNYLATED PHENYLBENZIMIDAZOLE COMPOUNDS

This is a division of application Ser. No. 655,009, filed Sept. 26, 1984, now U.S. Pat. No. 4,537,974.

BACKGROUND OF THE INVENTION

1. Field of the Invention

The present invention relates generally to high temperature, thermoset polymers. More particularly, the present invention relates to new ethynylated phenylbenzimidazole compounds, their use as prepolymers and their fabrication into polymer structures which are stable at high temperatures.

2. Description of the Background Art

In the past two decades there has been a great deal of interest in developing heterocyclic polymers which have sufficient thermo-oxidative stability to be useful at temperatures up to 371° C. (700° F.). Although many types of these high temperature polymers have been developed, most of them have not been sucessfully utilized in the production of hardware or produced on a commercial scale. The lack of commercialization of these polymers is due mainly to difficulties in processing. Generally, such polymers are highly intractable and cannot be effectively used in fabrication. Even when made in prepolymer form, they still pose the problem of generally liberating gaseous by-products when they undergo further polymerization by condensation.

Five typical polymers of the general type mentioned above are: poly[benzobis(triazolo)phenanthroline]; poly[(7-oxo-7,1OH-benz[d,e]imidazo[4',5':5,6]benzimidazo[2,1a]isoquinoline-3,4,10,11-tetryl)-10-carbonyl] (commonly called BBL); poly[bis(benzimidazo)benzophenanthroline] (commonly called BBB); polybenzimidazoquinazoline (generally referred to as PIQ); and polynaphthalimide. These materials represent some of the most stable polymers known. Other heterocyclic polymers such as polybenzoxazoles, polybenzimidazoles, and polybenzothiazoles are also well documented in the polymer literature and have been shown to have excellent thermal stability.

The preparation of thermosetting prepolymers of the above-discussed general classes of materials and the development of addition curing mechanisms for their polymerization could eventually provide useful commercial products. Their thermal stabilities are sufficiently close to each other that it would be very difficult to predict accurately which class would ultimately give the most useful thermoset resins, since many other variables must be considered. Accordingly, there is a continuing need to develop additional monomers which can be conveniently processed by commercial fabrication techniques into polymers which exhibit the high temperature stability of the above-mentioned compounds.

Various acetylene-substituted compounds have been shown to homopolymerize by the application of heat or a catalyst to form resins which are stable at high temperatures. As a result, practical thermosetting acetylene-substituted prepolymers have begun to appear in the literature. These acetylene-terminated prepolymers have shown promise since they provide high-temperature thermosets which cure without the evolution of gaseous by-products and could eventually yield fabricated structures having excellent thermal and mechanical properties. However, the early introduction of an acetylene-substituted resin, Haveg-H-resin (Hercules, Inc.), met with very limited success, mainly because of the relatively small processing window and the poor long-term high-temperature oxidative stability of the cured product.

Thermosetting polyimide oligomers have also been considered as possible useful high temperature resins due to the excellent thermal stability inherent in the polyimide backbone. A series of acetylene-terminated polyimide prepolymers has been developed which is soluble in an acceptable common solvent and tractable in imidized form. These prepolymers were subsequently marketed as Thermid 600 by Gulf Oil and Chemical Company.

Other acetylene or ethynyl terminated oligomers such as acetylene-terminated phenylquinoxalines have been under development. These prepolymers are also thermosetting and can be cured to provide moisture-resistant products of very high thermo-oxidative stability. The oligomers have many properties desirable for processing, i.e., high solubility in low-boiling-point aprotic solvents, low softening temperature prior to cure, a wide temperature difference between the melting and cure temperatures, cure without the evolution of gaseous products, and after cure, glass transition temperature sufficiently high (310°–350° C.) to allow long-term use at 250° C. Relative advantages of the various types of acetylene-terminated polyquinoaxlines have not been fully determined, although mechanical property data have been collected.

Another acetylene-terminated prepolymer which is receiving considerable attention is bis[4-(3-ethynylphenoxy)phenyl]sulfone. This material has been evaluated as a polymerizable plasticizer for various thermoplastics.

As is apparent from the discussion above, numerous different acetylene-terminated monomers have been developed which are suitable in varying degrees for use in fabricating high temperature resins. Even so, there is still a continuing need to develop new classes of acetylene-terminated compounds which are easily and conveniently fabricated to provide addition-curing processible matrix resins having a service temperature capability of 350° C.

SUMMARY OF THE INVENTION

In accordance with the present invention, a new benzimidazole monomer compound has been discovered which can be processed into high temperature polyphenylbenzimidazole polymers which are stable at temperatures above 300° C.

The present invention is based on a diethynylated bisbenzimidazole monomer having the formula:

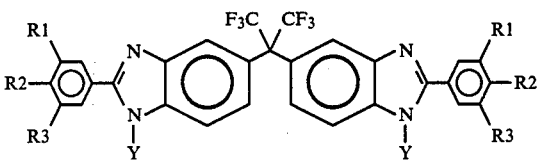

where Y is phenyl, cyclohexyl, adamantyl or phenoxylatedphenyl of the formula $C_6H_5(OC_6H_4)_n$ (n=1 to 3) and where R1, R2 and R3 are ethynyl, phenoxyethynyl, phenylethynyl or hydrogen.

As one aspect of the present invention, a prepolymer, which consists essentially of oligomers of compounds in accordance with the present invention, is provided which may be heat cured to provide a polymer product which is easily fabricated and remains stable at relatively high temperatures. The invention also includes the polymers produced either directly from the monomer or by way of a prepolymer.

The present invention provides a new benzimidazole monomer and oligomer compositions which are more tractable and easier to handle and process than prior high temperature resin precursors, while still providing a polymer product having good high temperature stability.

The above-discussed and many other features and attendant advantages of the present invention will become apparent as the invention becomes better understood by reference to the following detailed description when considered in conjunction with the accompanying drawing.

BRIEF DESCRIPTION OF THE DRAWING

The drawing is a schematic outline of the synthesis of an exemplary preferred compound in accordance with the present invention.

DETAILED DESCRIPTION OF THE INVENTION

The present invention involves the synthesis of a new benzimidazole monomer having the general formula:

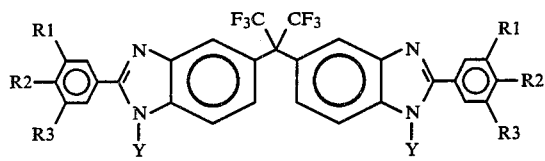

where Y is pheynl, cyclohexyl, adamantyl or phenoxylatedphenyl of the formula $C_6H_5(OC_6H_4)n$ (n=1 to 3) and R1, R2 and R3 are ethynyl, phenyoxyethynyl, phenylethynyl or hydrogen.

Preferably, only one of R1, R2 or R3 is ethynyl or an ethynyl derivative for a given compound with the two other remaining R groups being hydrogen. Although compounds in accordance with the present invention include those having ethynyl groups at both the para- and meta-positions, these compounds are more difficult to make than those having only a single ethynyl, phenyoxyethynyl or phenylethynyl group attached at the meta (R1 and R3) or para (R2) positions. Accordingly, the following description will be limited to those monomers in which hydrogen is present at two of the three R1, R2 and R3 positions.

A preferred monomer is one in which R1 or R3 is ethynyl and the remaining two R groups (i.e., either R1 or R3, and R2) are hydrogen and Y is phenyl. Preparation and use of this preferred compound is shown in the drawing and discussed in detail below. In another preferred compound, the ethynyl group is positioned at the para-position (R2) instead of the meta-position (R1 or R3). Preparation of this compound is also set forth in the following examples.

In addition to phenyl groups, bridged compounds such as adamantane may be incorporated into the monomer by attachment as an adamantyl group at the Y position to increase the rigidity of the polymer product and to enhance the basicity of the nitrogen atom to which the adamantyl group is attached. Saturated cycloalkanes, such as cyclohexane may be attached at the Y position as well as phenoxylated phenyl pendants of the formula $C_6H_4(OC_6H_4)n$ (n=1, 2, or 3). It is preferred that n=1; however, when desired to provide added flexibility to the polymer, 2 or 3 phenyoxyphenyl groups may be attached at the Y site (i.e., n=2 or 3).

The monomers in accordance with the present invention may be handled in accordance with conventional fabrication and processing techniques used for polybenzimidazole (PBI) and other thermoset polymers. Preferably, prepolymer solutions consisting essentially of oligomers of the monomer are prepared and then heat cured according to conventional techniques to provide a polymer product which is useful as a high temperature polymer. The polymer products have been shown to be stable at temperatures above 300° C.

Examples of practice are as follows.

EXAMPLE 1

5,5'-(hexafluoroisopropylidine)bis[1-phenyl-2-(3-ethynylphenyl)benzimidazole] (Compound VIII)

The synthesis of Compound VIII as an exemplary compound in accordance with the present invention is schematically shown in the drawing. The synthesis basically involves a condensation reaction between 3-(trimethylsilylethynyl)benzaldehyde (VI) and 2,2-bis(3-amino-4-anilinophenyl)hexafluoropropane (V).

EXAMPLE 1A 3-(trimethylsilylethynyl)benzaldehyde (Compound VI)

Compound VI was synthesized by the organopalladium-catalyzed ethynylation of meta-bromobenzaldehyde with ethynyltrimethylsilane as follows:

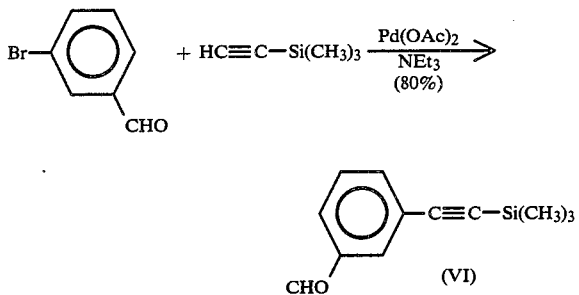

The details of preparation of compound VI are set forth in a publication by W. B. Austin, N. Bilow, W. J. Kelleghan and K. S. Y. Lau in the *Journal of Organic Chemistry*, Vol. 46, p. 2280 et seq., (1981), the contents of which is hereby incorporated by reference. The compound (VI) was synthesized with an 80% yield and had the following properties: bp 120°-122° C./0.15 torr; IR (film): 2958, 2146, 1692, 1244, and 843 cm$^{-1}$; MS m/e 202 (molecular ion), 187; NMR (CDCl$_3$): δ0.22 (s, 9H, SiCH$_3$), 7.15-9.93 (m, 4H, aromatic), and 9.85 ppm (s, 1H, CHO).

Analysis: Calculated for $C_{12}H_{14}OSi$: C, 71.24%: H, 7.33%; Si, 13.88%. Found: C, 71.10%; H, 7.07%; Si, 14.04%.

Nuclear magnetic resonance (NMR) spectra were taken on a Varian EM-360L spectrometer with tetramethylsilane (TMS) as the internal standard. Infrared (IR) spectra were taken on a Beckman IR-5 spectrometer. Mass spectra (MS) were measured by West Coast Tech-

EXAMPLE 1B 2,2-Bis(3-amino-4-anilinophenyl)hexafluoropropane (Compound V)

Compound V was prepared from 2,2-bis(4-hydroxyphenyl)hexafluoropropane (I) according to the four-step synthetic sequence outlined in the drawing. The details of the synthesis are set forth in an article by K. S. Y. Lau, A. L. Landis, W. J. Kelleghan, and C. D. Beard in the *Journal of Polymer Science, Polymer Chemistry Edition*, Vol, 20, p. 2381 et seq., (1982), the contents of which is hereby incorporated by reference. An overall yield of 89.3% was obtained with the compound having the following properties:

Mp 120° C.; IR (KBr): 3380 (strong, broad, $NH_2$), 1620, 1600, 1520, 1500 (strong, sharp, C=N and C=C), and 1310–1160 $cm^{-1}$ (strong, very broad, $CF_3$); NMR (acetone-$d_6$): δ2.90 (bs, 3H, NH) and 6.35–7.42 ppm (m, 8H, aromatic).

Analysis: Calculated for $C_{27}H_{22}F_6N_4$: C, 62.79%; H, 4.29%; N, 10.85%; F, 22.01%. Found: C, 62.61%; H, 4.26%; N, 10.70%; F, 22.15%.

EXAMPLE 1C 5,5'-(hexafluoroisopropylidene)bis[1-phenyl-2-(3-ethynylphenyl)benzimidazole] (Compound VIII)

Compound VIII was synthesized from compounds (VI) and (V) as follows. A mixture of 2.00 g of sodium metabisulfite and 0.76 g (4.26 mmol) of 3-(trimethylsilylethynyl)benzaldehyde (VI) in 50 ml of 1:1 ethanol-water was deaerated with argon and heated at 75°–80° C. for 30 minutes. The yellow solution was then treated with a slurry of 1.00 g (1.94 mmol) of 2,2-bis(3-amino-4-anilinophenyl)hexafluoropropane (V) in 50 ml of ethanol. The mixture was heated at a gentle reflux (oil bath temperature about 100° C.) for 7 hours, cooled, diluted with 100 ml of 10% hydrochloric acid. The bright yellow solid was filtered, then washed with 50 ml of 10% hydrochloric acid, 50 ml of water and 50 ml of cold hexane. The powdery product (VII), after thorough drying, weighed 1.67 g (1.90 mmol, 97.8%) and showed characteristic trimethylsilylethynyl absorptions in its infrared spectrum.

The above product (VII) (1.36 g, 1.55 mmol) was treated with 100 mg of anhydrous potassium carbonate in 50 ml of methanol under argon for 24 hours. The mixture was concentrated, dissolved in 50 ml dichloromethane, and washed with 50 ml of 10% hydrochloric acid. The organic phase was dried over magnesium sulfate and concentrated; the residue was triturated with cold hexane to yield 1.02 g (1.39 mmol, 89.5%) of a powdery solid. The product was purified by column chromatography using 1:1 dichloromethane-hexane as eluant. Infrared spectra indicated IR (KBr): 3500–3000, 3300, and 2120 $cm^{-1}$.

EXAMPLE 2

Scaled up Synthesis of 5,5'-(hexafluoroisopropylidene)bis[1-phenyl-2-(3-ethynylphenyl)benzimidazole] (Compound VIII)

Synthesis of the above compound (VIII) was scaled up to a quarter-molar-scale to demonstrate the feasibility of larger scale production. Except for the scaleup proportions, the procedure as set forth below, was identical to the synthesis described above.

A mixture of 115 g (0.570 mol) of 3-(trimethylsilylethynyl)benzaldehyde and 216 g (1.14 mol) of sodium metabisulfite in 2 L of 1:1 ethanol-water was heated at 70°–80° C. for 1 hour and mixed with 110.6 g (0.214 mol) of 2,2-bis(3-amino-4-anilinophenyl)hexafluoropropane in 1 L of ethanol. The mixture was stirred at reflux for 24 hours. The mixture after cooling was diluted with 6 L of 5% aqueous hydrochloric acid. Filtration, washing with water, and thorough drying yielded a total of 182.5 g (0.207 mol, 96.9%) of a powdery solid which showed the characteristic infrared absorptions for the trimethylsilylethynyl groups.

The crude product was dissolved in 1.5 L of absolute methanol and treated with 10 g of anhydrous potassium carbonate. The initial dark brown solution slowly yielded a yellowish precipitate. After being stirred for 60 hours at 25° C., the mixture was diluted with an equal volume of 5% hydrochloric acid and filtered, and the solid was air dried thoroughly.

The first crop (90 g crude yield) was filtered through a preparative column of silica gel with 2:1 hexane-dichloromethane as eluant. The column-purified end product was pale yellow and powdery and gave a combustion analysis acceptable for the desired prepolymer. Infrared analysis showed the characteristic ethynyl end groups (3300, 2120 $cm^{-1}$).

Analysis: Calculated for $C_{45}H_{26}F_6N_4 \cdot H_2O$: C, 71.61%; H, 3.74%; F, 15.10%; N, 7.42%. Found: C, 71.75%; H, 3.86%; F, 14.92%; N, 7.37%.

The observed gel time at 250° C. on the Kofler hot bench was significantly shorter (about 1 minute) for the scaleup batch than for that synthesized on a small scale (3–4 minutes). Thin-layer chromatography suggested that higher oligomers were present. Washing of the column-purified powder with ether separated the ether-insoluble portion, which was probably mostly higher oligomeric material. No melting was observed even at 275° C. The ether-soluble portion gave an observed gel time at 250° C. of about 1 minute.

EXAMPLE 3

Alternate method of synthesizing 5,5'-(hexafluoroisopropylidene)bis[1-phenyl-2-(3-ethynylphenyl)benzimidazole] (Compound VII)

An alternate method of synthesizing Compound VII is as follows. A solution of 6.0 g of sodium metabisulfite in 75 ml of water was mixed with 2.58 g (14.0 mmol) of 3-(trimethylsilylethynyl)benzaldehyde (VI) in 125 ml of ethanol, deaerated with argon, and heated to reflux over 15 minutes. The mixture was heated at reflux for 30 minutes and then treated by dropwise addition with a solution of 3.00 g (5.81 mmol) of 2,2-bis(3-amino-4-anilinophenyl)hexafluoropropane (V) in 250 ml of ethanol. After complete addition (1 hour), the mixture was heated at reflux for 24 hours. The mixture was then cooled, stirred into 1 L of 10% hydrochloric acid, and filtered. The powdery solid (VII) after thorough drying, weighed 5.10 g (5.80 mmol, 99.7%). Characteristic infrared absorptions of the trimethylsilylethynyl groups were exhibited.

The crude product (VII) was treated with 1 g of anhydrous potassium carbonate in 100 ml of methanol at 25° C. for 24 hours. The solvent was removed and the residue thoroughly washed with 10% hydrochloric acid and air dried. The powdery end product (VIII)

was washed with ether to yield ether-soluble and ether-insoluble fractions. The ether-insoluble fraction did not melt at 250° C. The ether-soluble fraction gave a lustrous yellow powdery material; yield 2.5 g (58.4%); at 230°, 240°, and 250° C., this material melted to a fluid which resolidified in about 3 minutes. The ether-soluble and the ether-insoluble fractions have superimposable IR spectra showing the characteristic ethynyl end-group absorptions (3300, 2100 cm$^{-1}$).

The exact procedure described above (high dilution and dropwise addition) was repeated for 26.0 g of the aldehyde (VI), 110 g of sodium bisulfite, and 30.0 g of the tetramine (V) in a total volume of 4.5 L of 1:5 water-ethanol. At the end, the powdery end product (VIII) was fractionated by Soxhlet extraction into an ether-insoluble portion (high oligomers) and an ether-soluble portion (20.0 g, 46.9%). The latter material, when tested on the Kofler hot bench at 250° C., showed a gel time of about 3 minutes.

EXAMPLE 4

5,5'(hexafluoroisopropylidene)bis[1-phenyl-2-(4-ethynylphenyl)benzimidazole] (Compound IX)

Compound IX was prepared as a second exemplary compound in accordance with the present invention. Compound IX is the same as compound VIII except that the ethynyl groups are located at the para-position instead of the meta-position as indicated in the following structural formula:

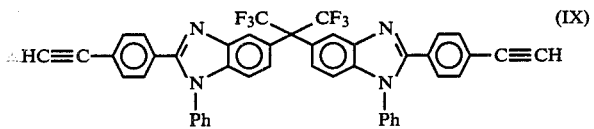

Preparation of compound IX is basically the same as preparation of compound VIII except that 4-(trimethylsilylethynyl)benzaldehyde is used in the condensation reaction instead of 3-(trimethylsilylethynyl)benzaldehyde (VI).

EXAMPLE 4A 4-(trimethylsilylethynyl)benzaldehyde

Preparation of 4-(trimethylsilylethynyl)benzaldehyde is described in detail in the previously referenced article and is basically the same as the preparation of compound (VI) described herein, except that para-bromobenzaldehyde is ethynylated. The 4-(trimethylsilylethynyl)benzaldehyde for this example was prepared according to the above-referenced procedure and provided a 99% yield. The physical properties of the compound were:

Mp 66°-67° C.; IR (KBr): 2960, 2825, 2720, 2145, 1690, 1245, and 840 cm$^{-1}$, MS m/e 202 (molecular ion), 187; NMR (CDCl$_3$): 0.21 (s, 9H, Si—CH$^3$), 7.60 (q, 4H, J=7.0 Hz, aromatic), and 9.85 ppm (s, 1H, CHO).

Analysis: Calculated for C$_{12}$H$_{14}$OSi: C, 71.24%; H, 7.33%; Si, 13.88%. Found: C, 71.31%; H, 7.42%; Si, 14.01%.

EXAMPLE 4B 5,5'(hexafluoroisopropylidene)bis[1-phenyl-2-(4-ethynylphenyl)benzimidazole] (Compound IX)

A mixture of 0.64 g (3.20 mmol) of 4-(trimethylsilylethynyl)benzaldehyde and 1.98 g of sodium metabisulfite in 25 ml deionized water and 30 ml ethanol was deaerated with argon, heated to about 75° C., and held at that temperature for 30 minutes. A solution of 0.83 g (1.61 mmol) of 2,2-bis(3-amino-4-anilinophenyl)hexafluoropropane (V) in 35 ml of ethanol was added dropwise. The resulting mixture was heated at 75° C. for 6.5 hours and at 90° C. for 3 hours, cooled, and diluted with 50 ml of water. The solids isolated were extracted with 3×100 ml of hexane; the extracts were combined and washed with 10% hydrochloric acid and then with water. After drying over magnesium sulfate, the solution was concentrated to yield a bright yellow compound which softened at about 140° C. and melted at about 200° C. Infrared analysis indicated characteristic absorptions due to the trimethylsilylethynyl groups (3000, 2160, 1200, 850 cm$^{-1}$).

The crude product was treated with 100 mg of anhydrous potassium carbonate in 100 ml of methanol under argon. After being stirred for 16 hours, the mixture was concentrated and the residue was dissolved in 50 ml dichloromethane and extracted with 50 ml of 5% hydrochloric acid. The organic phase was dried over magnesium sulfate, concentrated, and purified by column chromatography on silica gel, using 1:1 dichloromethanehexane as eluant. The off-white microcrystalline solid (IX) weighed 1.10 g (1.49 mmol, 92.6%); m; 265° C. (melted and resolidified within seconds); IR (KBr): 3500-3000 and 2120 cm$^{-1}$.

Analysis: Calculated for C$_{45}$H$_{26}$F$_6$N$_4$.H$_2$O: C, 71.61%; H, 3.74%; F, 15.10%; N, 7.42%. Found: C, 71.57%; H, 3.89%; F, 15.15%; N, 7.38%.

EXAMPLE 5

5,5'-(hexafluoroisopropylidene)bis[1-(4-phenoxyphenyl)-2-(3-ethynylphenyl)benzimidazole] (Compound X)

Compound X was prepared as a third exemplary compound in accordance with the present invention. The compound is the same as compound VIII except that phenoxyphenyl is substituted for phenyl on the imidazole group (Y=phenoxyphenyl and n=1), as indicated in the following structural formula:

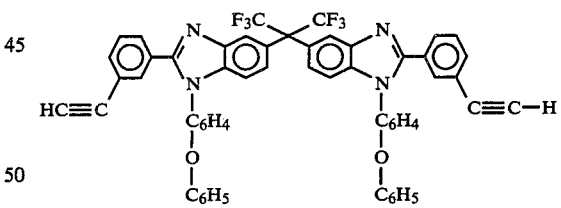

Compound (X) was prepared as follows.

A deaerated mixture of 4.75 g (25.0 mmol) of sodium metabisulfite and 2.04 g (10.0 mmol) of 3-(trimethylsilylethynyl)benzaldehyde (VI) in 150 ml of 50% aqueous ethanol was heated to 75° C. over 15 minutes. A solution of 3.20 g (4.58 mmol) of 2,2-bis[3-amino-4-(4-phenoxyanilino)phenyl]hexafluoropropane (XI) in 90 ml of absolute ethanol was added dropwise from an addition funnel while the reaction mixture was stirred at 80°-85° C. Details of the preparation of compound XI are also set forth in the article which was previously referenced in connection with the preparation of compound V.

The addition was controlled carefully so that it took 1.5 hours to complete. At the end, 50 ml more of ethanol was added. The mixture was stirred under argon at 85°–90° C. for 1 hour. After 48 hours, the reaction mixture was cooled and was treated with 250 ml of 10% hydrochloric acid. The milky suspension was extracted with 4×100 ml of dichloromethane. The combined dichloromethane extracts were washed with 150 ml of water containing 10 g of sodium bicarbonate, and with 150 ml of water, and then were dried over magnesium sulfate. Removal of the solvent left a light brown oil which, upon trituration with hexane, gave a pale yellow solid. NMR analysis of a solution of this product in acetone-$d_6$ showed that the ratio of SiCH$_3$ ($\delta$0.1 ppm) to aromatic ($\delta$6.80–8.00 ppm) was 19.7/34.3(0.57), which agreed with the theoretical value of 18/32(0.56). Infrared analysis showed the expected absorptions characteristics of trimethysilyl groups (2960, 2160, 1250, and 840 cm$^{-1}$). The pale yellow solid obtained was dissolved in 40 ml of anhydrous methanol, to which 1 g of anhydrous potassium carbonate was then added. The mixture was stirred at 25° C. for 24 hours before being treated with 50 ml of 10% hydrochloric acid. The gummy precipitate obtained was vigorously agitated until it appeared powdery. The solid was filtered and recrystallization from 50 ml of 1:2 dichloromethanehexane; yield 3.04 g (72.5% from the tetraamine). The product was further purified by column chromatography through a silica gel column, eluting with dichloromethane. Infrared spectra indicated IR (KBr): 3450, 3310, (strong C≡CH), 3080, 2160 (weak C≡C), 1590, 1510, 1490, and 1250–1200 cm$^{-1}$; NMR (Acetone-$d_6$): $\delta$3.60 (2H, C≡CH), and 6.95–8.00 ppm (m, 32H, aromatic).

Analysis: Calculated for C$_{57}$H$_{34}$N$_4$F$_6$O$_2$.H$_2$O): C, 72.92%; H, 3.94%; F, 12.14%; N, 5.97%. Found: C, 72,82%; H, 3.74%; F, 12.27%; N, 5.78%.

The melt behavior of the product was observed on the Kofler hot bench. Melting was observed at a temperature as low as 150° C. The gel times measured on milligram batches were 4 minutes at 210° C., 5 minutes at 170° C., 6.5 minutes at 160° C., and 10.5 minutes at 150° C.

EXAMPLE 6

Polymerization of prepolymers

Examples of preparation and fabrication of prepolymers and polymers from the above-described compounds are as follows.

A first large batch (quarter-molar scale) of prepolymer (VIII) was synthesized as previously described. This first scaleup of compound VIII, as also previously mentioned, had a short gel time (1 minute). The material had IR, NMR, and combustion analyses that were indistinguishable from the previously prepared smaller batch of VIII, so it was concluded that either higher-molecular-weight oligomeric material was present in the scaleup product or that there was an undefined operator variable.

In order to reduce the quantity of this oligomeric material, if it was in fact present, the condensation reaction of compound V with aldehyde was rerun at higher dilution as set forth in the alternate method for preparing compound VIII (supra). Subsequent conversion of this second batch of compound VIII resulted in a quite acceptable prepolymer, based upon its significantly longer gel time.

Preliminary neat resin gel time studies and prepreg fabrication were performed on prepolymers VIII. The first batch (from the small scale synthesis) of VIII showed an initial melting range of 225°–230° C., and changed to a molasses-like consistency, remaining soft for 6–8 minutes before hardening into the cured polymer. The latter remelted to a fluid at 240° C. At 246°–250° C., the fluid hardened within 4.5–5.0 minutes. At 260° C., the gel time was 3.5 minutes. The neat resin was molded into button specimens. The specific gravity was measured to be 1.28. The glass transition temperature (Tg) after 16-hour postcure at 316° C. was 311° C.; Tg after 16-hour postcure at 371° C. was 344° C.

The results of gel time studies on the first scaleup batch of VIII were 2.5–3.0 minutes at 250° C. and 1.5 minutes at 260° C., which indicated that this batch contained oligomers of higher degree of polymerization (DP) than the previous batch.

The N-phenoxy-substituted diethynylated bisbenzimidazole prepolymer (X) showed good potential processibility. On the temperature-calibrated hot bench, it became fluid at temperatures below 170° C. and, at these temperatures, appeared to remain fluid for about 8–10 minutes. An 8 g batch of prepolymer (X) was prepared for preliminary neat resin evaluation. This batch of material began to soften at a temperature as low as 116° C. At 170° C., it developed a molasses-like consistency and remained soft over 8 minutes. At 200° C., it melted to a fluid, remained fluid over 8 minutes, and resolidified after 10 minutes. At 250° C., it melted to a fluid and resolidified within 3.5 minutes. At 261° C., it still had a gel time of 35–45 seconds. After prepolymer (X) was further purified by column chromatography, it became a fluid even below 170° C. and rehardened after 10 minutes. The polymer of (X) appears slightly soluble in acetone after a short (40±5 seconds) "cure" at 261° C.; it was very slightly soluble in acetone after 4 hours at 316° C., and was insoluble in acetone after 14 hours at 320° C. Although an 8 minute gel time at 200° C. is an encouraging result, the fact that the polymerization exotherm reaches a maximum at 235° C. indicates that real-time processing will have to be carried out at a temperature of 235° C. or higher at which temperature the gel time is much shorter. The processing characteristics of prepolymer (X) appear to be better than those for prepolymers made from compound VIII. Accordingly, the (X) prepolymer is a preferred embodiment.

Having thus described exemplary embodiments of the present invention, it should be noted by those skilled in the art that the within disclosures are exemplary only and that various other alternatives, adaptations and modifications may be made within the scope of the present invention. Accordingly, the present invention is not limited to the specific embodiments as illustrated herein, but is only limited by the following claims.

What is claimed is:

1. A polymer composition consisting essentially of polymerized monomers having the formula:

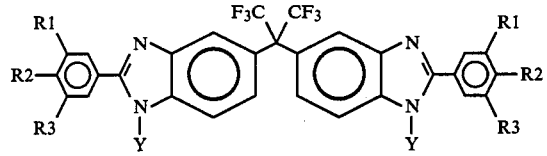

where Y is phenyl, cyclohexyl, adamantyl or phenoxylatedphenyl of the formula C$_6$H$_5$(OC$_6$H$_4$)n (n=1 to 3) and where R1, R2 and R3 are ethynyl, phenoxyethynyl, phenylethynyl or hydrogen, and further wherein at least one of said R1, R2 or R3 is not hydrogen.

2. A polymer composition according to claim 1 wherein R1 is hydrogen, R2 is hydrogen, R3 is ethynyl, Y is phenoxylatedphenyl, and n=1.

3. A polymer composition according to claim 1 wherein R1 is hydrogen, R2 is hydrogen, R3 is ethynyl, and Y is phenyl.

* * * * *